US012810416B2

(12) United States Patent
Gulsun et al.

(10) Patent No.: US 12,810,416 B2
(45) Date of Patent: Nov. 24, 2026

(54) TRAINING AI SYSTEMS ON PHOTON COUNTING DATA

(71) Applicant: Siemens Healthineers AG, Forchheim (DE)

(72) Inventors: Mehmet Akif Gulsun, Princeton, NJ (US); Puneet Sharma, Princeton Junction, NJ (US); Max Schöbinger, Hirschaid (DE)

(73) Assignee: Siemens Healthineers AG, Forchheim (DE)

( * ) Notice: Subject to any disclaimer, the term of this patent is extended or adjusted under 35 U.S.C. 154(b) by 426 days.

(21) Appl. No.: 18/346,292

(22) Filed: Jul. 3, 2023

(65) Prior Publication Data

US 2025/0014174 A1 Jan. 9, 2025

(51) Int. Cl.
*G06T 7/00* (2017.01)
*G16H 30/40* (2018.01)
*G16H 50/20* (2018.01)

(52) U.S. Cl.
CPC ........... *G06T 7/0012* (2013.01); *G16H 30/40* (2018.01); *G16H 50/20* (2018.01); *G06T 2207/10081* (2013.01); *G06T 2207/20081* (2013.01); *G06T 2207/20084* (2013.01); *G06T 2207/30004* (2013.01)

(58) Field of Classification Search
CPC ....... A61B 6/4241; A61B 6/032; A61B 6/482; A61B 6/5211; A61B 6/5217; A61B 6/03; G06T 2207/10081; G06T 7/0012; G06T 11/008; G06T 2210/41; G06T 2211/441; G06T 2207/20084; G06T 2207/30004; G06T 11/005; G06T 2207/20081; G06N 3/08; G06N 3/096; G16H 50/20; G16H 30/00; G16H 30/40; G16H 30/20; G06V 10/82; G06V 2201/031; G06V 2201/03
See application file for complete search history.

(56) References Cited

U.S. PATENT DOCUMENTS

| | | | |
|---|---|---|---|
| 8,965,095 | B2 | 2/2015 | Zou et al. |
| 10,853,449 | B1 | 12/2020 | Nguyen et al. |
| 11,556,784 | B2 | 1/2023 | Luo et al. |

(Continued)

FOREIGN PATENT DOCUMENTS

| | | | | |
|---|---|---|---|---|
| CN | 110879949 B | 4/2023 | | |
| EP | 3695784 A1 * | 8/2020 | .......... | A61B 6/5217 |
| WO | 2014192935 A1 | 12/2014 | | |

OTHER PUBLICATIONS

Arritt, Robert P. et al.: "Context-sensitive weights for a neural network." International and Interdisciplinary Conference on Modeling and Using Context. Berlin, Heidelberg: Springer Berlin Heidelberg, 2003. (Year: 2003).

(Continued)

*Primary Examiner* — Courtney Joan Nelson

(57) ABSTRACT

Systems and methods for training a machine learning based network based on PCCT (photon counting computed tomography) imaging data. PCCT imaging data acquired from a PCCT imaging device is received. One or more PCCT virtual images are generated from the PCCT imaging data. A machine learning based network is trained for performing a medical imaging analysis task based on the one or more PCCT virtual images. The trained machine learning based network is output.

14 Claims, 9 Drawing Sheets

(56) References Cited

U.S. PATENT DOCUMENTS

| | | | | |
|---|---|---|---|---|
| 2018/0018757 | A1* | 1/2018 | Suzuki | A61B 6/5205 |
| 2019/0354850 | A1* | 11/2019 | Watson | G06N 5/02 |
| 2020/0074629 | A1 | 3/2020 | Zur | |
| 2020/0297299 | A1 | 9/2020 | Hofmann et al. | |
| 2022/0287668 | A1 | 9/2022 | Gulsun et al. | |
| 2022/0366679 | A1* | 11/2022 | Li | G06T 7/11 |
| 2023/0116897 | A1* | 4/2023 | Hosseinzadeh Taher | G06V 10/774 382/156 |

OTHER PUBLICATIONS

U.S. Appl. No. 17/935,581, “CT Reconstruction for Machine Consumption”, filed Sep. 27, 2022, 37 pgs.

* cited by examiner

TRAINING AI SYSTEMS ON PHOTON COUNTING DATA

TECHNICAL FIELD

The present invention relates generally to AI (artificial intelligence)/ML (machine learning) for medical imaging analysis, and in particular to training AI/ML systems on photon counting data.

BACKGROUND

Photon counting is a technique in CT (computed tomography) imaging in which spectral imaging data is acquired by counting individual photons using energy-selective photon-counting detectors. Images may be generated from the spectral imaging data with high spatial resolution, without electronic noise, with improved contrast-to-noise ratio, and with spectral information.

Recently, AI/ML-based systems have been proposed for performing various medical imaging analysis tasks on medical images. However, there are no existing approaches for training AI/ML-based systems using images generated from spectral imaging data acquired via photon counting.

BRIEF SUMMARY OF THE INVENTION

In accordance with one or more embodiments, systems and methods for performing a medical imaging analysis task is performed using a trained machine learning based network trained based on PCCT (photon counting computed tomography) imaging data. One or more input medical images are received. A medical imaging analysis task is performed based on the one or more input medical images using a trained machine learning based network. Results of the medical imaging analysis task are output. The trained machine learning based network is trained by receiving PCCT imaging data acquired from a PCCT imaging device, generating one or more PCCT virtual images from the PCCT imaging data, training the machine learning based network for performing the medical imaging analysis task based on the one or more PCCT virtual images, and outputting the trained machine learning based network.

In one embodiment, the one or more PCCT virtual images comprise at least one of virtual monoenergetic images, virtual non-contrast images, virtual iodine images, virtual pure lumen images, and ultra-high-resolution images.

In one embodiment, the machine learning based network is trained based only on the one or more PCCT virtual images. In another embodiment, the machine learning based network is trained based on the one or more PCCT virtual images and non-photon-counting data. In a further embodiment, the machine learning based network is pre-trained based on non-photon-counting data and the pre-trained machine learning is fine-tuned based network based on the one or more PCCT virtual images.

In one embodiment, the one or more PCCT virtual images comprises a plurality of PCCT virtual images and the machine learning based network is trained based on a multi-channel image comprising the plurality of PCCT virtual images. In another embodiment, the one or more PCCT virtual images comprises a plurality of PCCT virtual images, the machine learning based network is pre-trained based on a multi-channel image comprising non-photon-counting data, and the pre-trained machine learning based network is fine-tuned based on a multi-channel image comprising the plurality of PCCT virtual images.

In one embodiment, the machine learning based network is trained for performing a plurality of medical imaging analysis tasks based on the one or more PCCT virtual images.

In accordance with one or more embodiments, systems and methods for training a machine learning based network based on PCCT (photon counting computed tomography) imaging data. PCCT imaging data acquired from a PCCT imaging device is received. One or more PCCT virtual images are generated from the PCCT imaging data. A machine learning based network is trained for performing a medical imaging analysis task based on the one or more PCCT virtual images. The trained machine learning based network is output.

These and other advantages of the invention will be apparent to those of ordinary skill in the art by reference to the following detailed description and the accompanying drawings.

DETAILED DESCRIPTION

The present invention generally relates to methods and systems for training AI/ML systems on photon counting data. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for training an AI/ML system for performing a medical imaging analysis task based on one or more PCCT (photon counting computed tomography) virtual images. The one or more PCCT virtual images may be, e.g., monoenergetic images reconstructed from different energy levels, non-contrast images, iodine images, pure lumen images, ultra-high-resolution images, etc. Advantageously, embodiments described herein provide for training AI/ML systems for performing a medical imaging analysis task based on one or more PCCT virtual images thereby improving performance the trained AI/ML systems.

Figure 1:
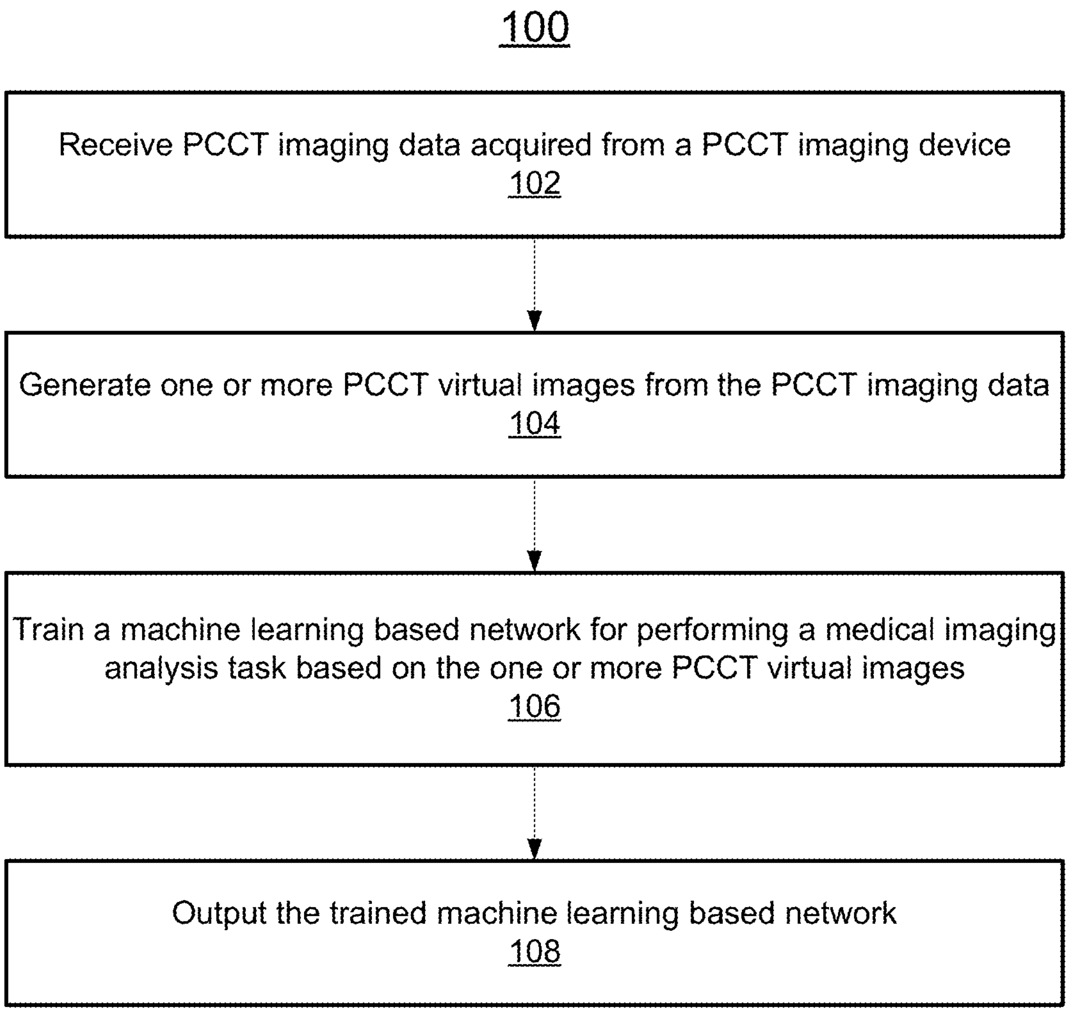
FIG. 1 shows a method for training a machine learning based network for performing a medical imaging analysis task based on PCCT (photon counting computed tomography) imaging data, in accordance with one or more embodiments.
Figure 2:
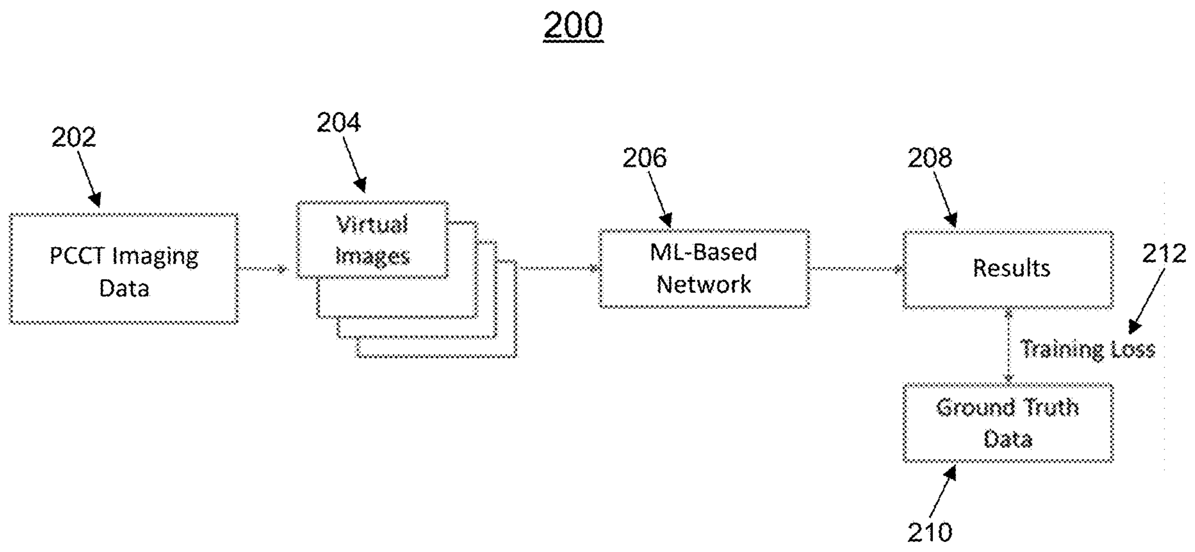
FIG. 2 shows a workflow for training a machine learning based network for performing a medical imaging analysis task based on PCCT imaging data, in accordance with one or more embodiments.

AI/ML systems are trained to perform a medical imaging analysis task using one or more PCCT virtual images during an offline or training stage, for example, according to method 100 of FIG. 1 or workflow 200 of FIG. 2. Once trained, the trained AI/ML systems may be applied to perform the medical imaging analysis task during an online or inference stage, for example, according to method 600 of FIG. 6.

FIG. 1 shows a method 100 for training a machine learning based network for performing a medical imaging analysis task based on PCCT imaging data, in accordance with one or more embodiments. The steps of method 100 may be performed by one or more suitable computing devices, such as, e.g., computer 902 of FIG. 9. FIG. 2 shows a workflow 200 for training a machine learning based network for performing a medical imaging analysis task based on PCCT imaging data, in accordance with one or more embodiments. FIG. 1 and FIG. 2 will be described together.

At step 102 of FIG. 1, PCCT imaging data acquired from a PCCT imaging device is received. The PCCT imaging device is equipped with a photon counting detector for counting the number of incoming photons from an x-ray and directly measuring photon energy. The PCCT imaging data may be imaging data of any anatomical object or objects of interest of a patient, such as, e.g., organs, bones, lesions, etc. In one example, as shown in workflow 200 of FIG. 2, the PCCT imaging data may be PCCT imaging data 202. The PCCT imaging data may be received directly from the PCCT imaging device as the PCCT imaging data is acquired, can be received by loading previously acquired PCCT imaging data from a storage or memory of a computer system, or by receiving the PCCT imaging data from a remote computer system.

At step 104 of FIG. 1, one or more PCCT virtual images are generated from the PCCT imaging data. In one example, as shown in workflow 200 of FIG. 2, the one or more PCCT virtual images are virtual images 204. The one or more PCCT virtual images may be generated from the PCCT imaging data using any suitable (e.g., known) approach. For example, virtual non-contrast, iodine or pure lumen images can be reconstructed through decomposition of materials such as iodine, calcium, and fat, or virtual monoenergetic images can be reconstructed based on weighting and combining different energy bins available in the spectral data. In addition, small pixel size of photon-counting detectors allows for acquiring ultra-high-resolution images with a slice thickness significantly smaller than the conventional CT.

The one or more PCCT virtual images may be of different types. For example, the one or more PCCT virtual images may comprise virtual monoenergetic images reconstructed from different energy levels (e.g., 50 or 100 keV (kiloelectron volt)), virtual non-contrast images, virtual iodine images, virtual pure lumen images that subtract calcium from contrast enhanced scans, ultra-high-resolution images, or any other suitable type of PCCT virtual images.

In one embodiment, the one or more PCCT virtual images may be enriched based on various acquisition and reconstruction protocol parameters, such as, e.g., reconstruction algorithm and convolution kernels.

At step 106 of FIG. 1, a machine learning based network is trained for performing a medical imaging analysis task based on the one or more PCCT virtual images. In one embodiment, as shown in workflow 200 of FIG. 2, the machine learning based network is ML-based network 206. ML-based network 206 is trained to perform a medical imaging analysis task by receiving as input one or more virtual images 204 and generating as output results 208 of the medical imaging analysis task. In one embodiment, as shown in FIG. 2, ML-based network 206 is trained with supervised learning by comparing results 208 with ground truth data 210 according to training loss 212. Ground truth data 210 may be any suitable type of ground truth data, such as, e.g., human expert annotations or pseudo ground truth data generated based on processed virtual images. For example, the pseudo ground truth data may comprise a thresholded virtual iodine image for ML-based network 206 for centerline or lumen segmentation. In another example, the pseudo ground truth data may be an output of an existing machine learning processing a PCCT virtual image. In another embodiment, ML-based network 206 may be trained with unsupervised/self-supervised learning. Specifically, the ML-based network can be trained to reconstruct one or more virtual images by using one or more different virtual images provided as input. For example, the network can be trained to reconstruct a virtual monoenergetic image with a certain keV (e.g., 100 keV) based on an input virtual monoenergetic image with a different keV (e.g., 70 keV).

The medical imaging analysis task may comprise any suitable imaging analysis task, such as, e.g., segmentation, detection, registration, etc. For example, in the context of coronary applications, the medical imaging analysis task may comprise at least one of coronary centerline tracing, lesion detection, segment labeling, lumen and outer wall segmentation for performing clinical tasks (e.g., automated CAD-RADS (coronary artery disease reporting and data system scoring)), detection and quantification of coronary plaque and fat, computation of CT-FFR (computed tomography fractional flow reserve), detection of stent and quantification of in-stent restenosis, and detection of bypass graft and assessment of graft patency.

Figure 3A:
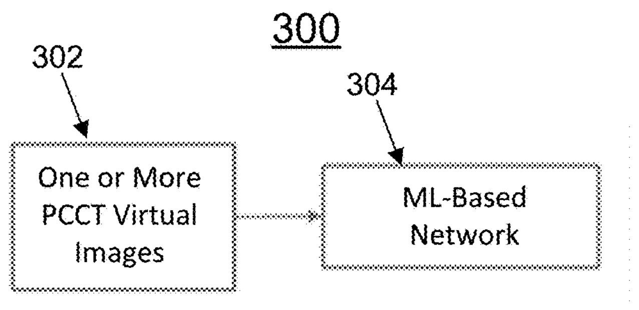
FIG. 3A shows a workflow for training a machine learning based network using only PCCT virtual images, in accordance with one or more embodiments.

In one embodiment, the machine learning based network is trained at step 106 of FIG. 1 using only the one or more PCCT virtual images (and not using non-photon-counting data). FIG. 3A shows a workflow 300 for training a machine learning based network using only PCCT virtual images, in accordance with one or more embodiments. As shown in FIG. 3A, ML-based network 304 is trained only using one or more PCCT virtual images 302.

Figure 3B:
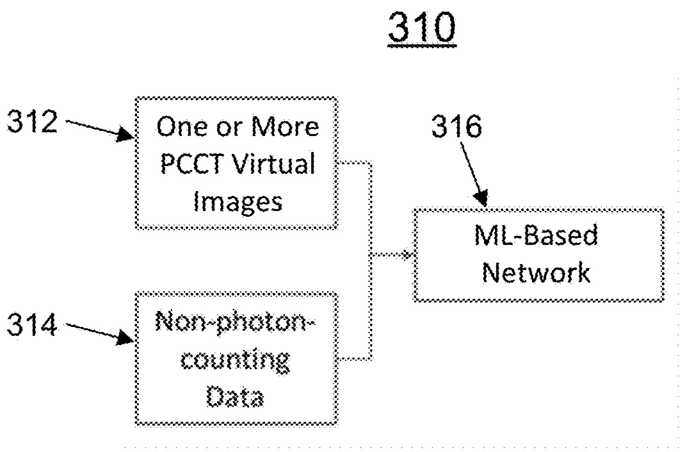
FIG. 3B shows a workflow for training a machine learning based network using both PCCT virtual images and non-photon-counting data, in accordance with one or more embodiments.

In one embodiment, the machine learning based network is trained at step 106 of FIG. 1 using one or more PCCT virtual images and non-photon-counting data. FIG. 3B shows a workflow 310 for training a machine learning based network using both PCCT virtual images and non-photon-counting data, in accordance with one or more embodiments. As shown in FIG. 3B, ML-based network 316 is trained using one or more PCCT virtual images 312 and non-photon-counting data 314. Non-photon-counting data 314 may comprise, for example in the coronary use case, angiogram, OCT (optical coherence tomography), and/or IVUS (intravascular ultrasound) images. Non-photon-counting data 314 may comprise any other suitable type of images, such as, e.g., CT (computed tomography) images, MRI (magnetic resonance imaging) images, ultrasound images, x-ray images, or images of any other medical imaging modality or combinations of medical imaging modalities. Non-photon-counting data 314 may be received at step 102 of FIG. 1.

Figure 3C:
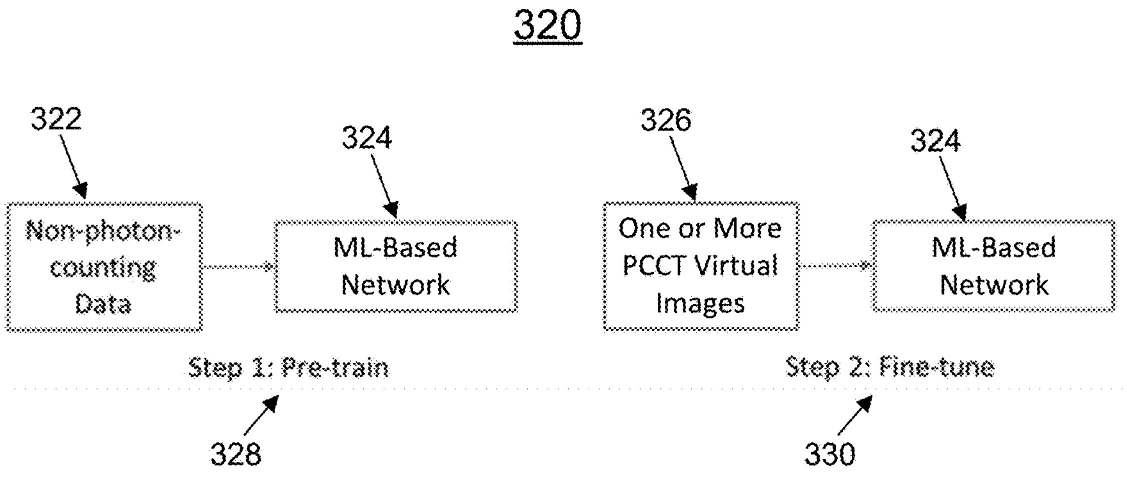
FIG. 3C shows a workflow for pre-training a machine learning based network using non-photon-counting data and fine-tuning the pre-trained machine learning based network using one or more PCCT virtual images, in accordance with one or more embodiments.

In one embodiment, the machine learning based network is pre-trained using non-photon-counting data and fine-tuned using one or more PCCT virtual images at step 106 of FIG. 1. FIG. 3C shows a workflow 320 for pre-training a machine learning based network using non-photon-counting data and fine-tuning the pre-trained machine learning based network using one or more PCCT virtual images, in accordance with one or more embodiments. As shown in FIG. 3C, during a pre-training step 328, ML-based network 324 is pre-trained using non-photon-counting data 322 (e.g., angiogram, OCT, IVUS, etc.) using, e.g., self-supervised learning. During a fine-tuning step 330, the pre-trained ML-based network 324 is fine-tuned using one or more PCCT virtual images 326.

Figure 4A:
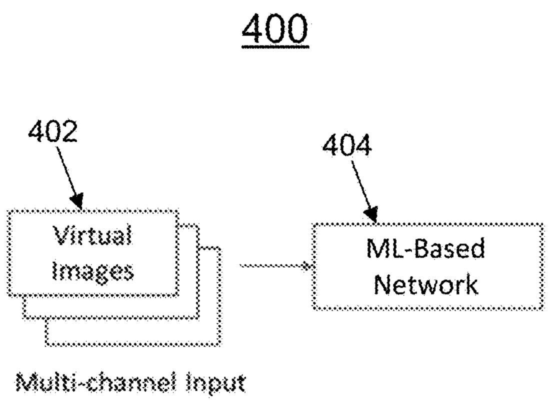
FIG. 4A shows a workflow for training a machine learning based network using a multi-channel PCCT virtual image, in accordance with one or more embodiments.

In one embodiment, the one or more PCCT virtual images comprises a plurality of PCCT virtual images and the machine learning based network is trained at step 106 of FIG. 1 using the plurality of PCCT virtual images combined into a single multi-channel image. FIG. 4A shows a workflow 400 for training a machine learning based network using a multi-channel PCCT virtual image, in accordance with one or more embodiments. A multi-channel image 402 is generated by combining the plurality of PCCT virtual images and ML-based network 404 is trained using multi-channel image 402 comprising the plurality of PCCT virtual images.

Figure 4B:
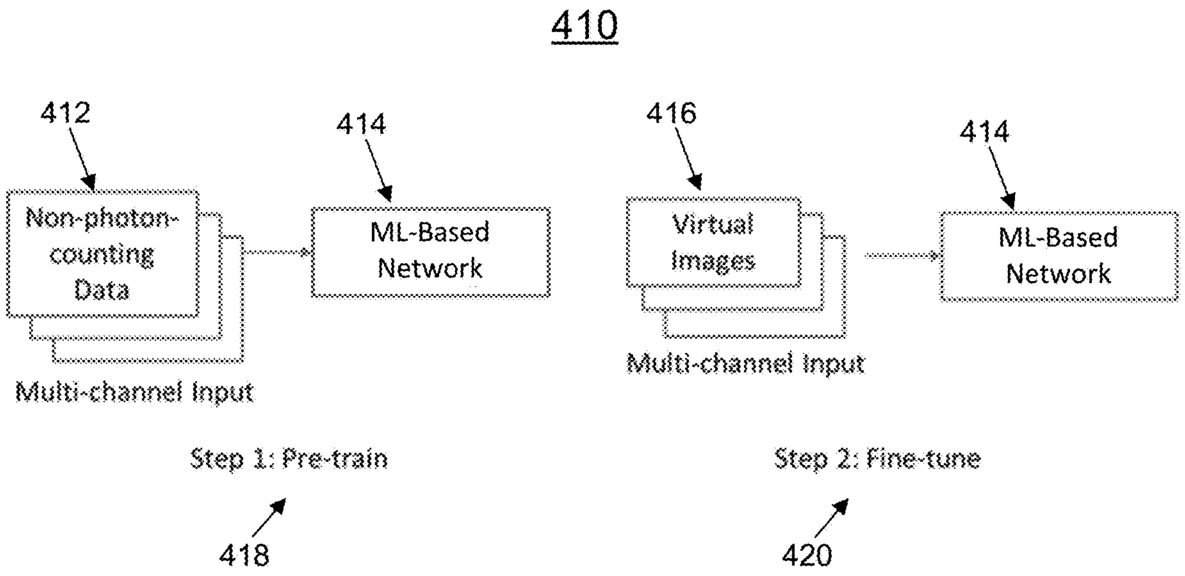
FIG. 4B shows a workflow for pre-training a machine learning based network using a multi-channel image comprising non-photon-counting data and fine-tuning the machine learning based network using a multi-channel image comprising a plurality of PCCT virtual images, in accordance with one or more embodiments.

In one embodiment, the one or more PCCT virtual images comprises a plurality of PCCT virtual images and the machine learning based network is pre-trained on a multi-channel image comprising non-photon-counting data and fine-tuned on a multi-channel image comprising a plurality of PCCT virtual images at step 106 of FIG. 1. FIG. 4B shows a workflow 410 for pre-training a machine learning based network using a multi-channel image comprising non-photon-counting data and fine-tuning the machine learning based network using a multi-channel image comprising a plurality of PCCT virtual images, in accordance with one or more embodiments. As shown in FIG. 4B, during a pre-training step 418, ML-based network 414 is pre-trained using a multi-channel image 412 comprising non-photon-counting data (e.g., angiogram, OCT, IVUS, etc.). During a fine-tuning step 420, the pre-trained ML-based network 414 is fine-tuned using a multi-channel image 416 comprising the plurality of PCCT virtual images.

At step 108 of FIG. 1, the trained machine learning based network is output. For example, the trained machine learning based network can be output by storing the trained machine learning based network on a memory or storage of a computer system or by transmitting the trained machine learning based network to a remote computer system. In one embodiment, the trained machine learning based network is output by deploying the trained machine learning based network, e.g., at a clinical site for use during an online or inference stage (e.g., according to method 600 of FIG. 6).

Figure 5:
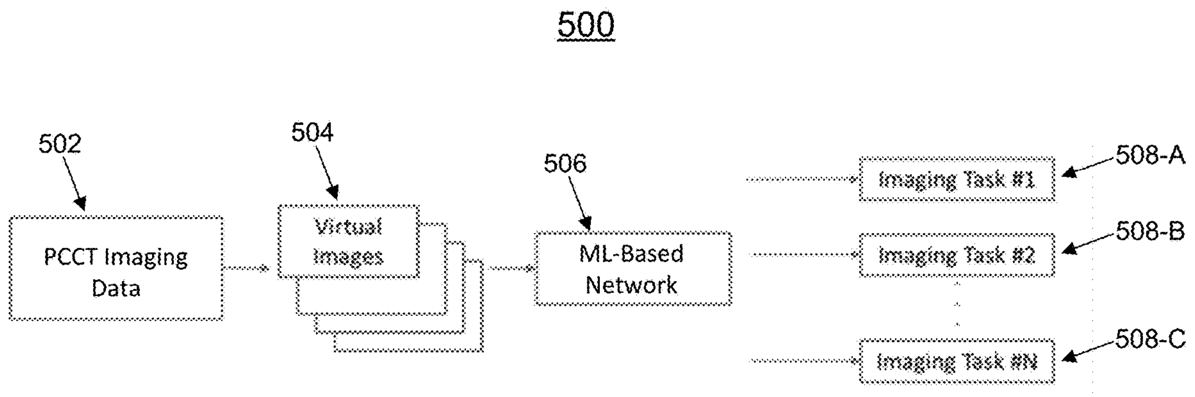
FIG. 5 shows a workflow for training a machine learning based network for performing a plurality of medical imaging analysis tasks based on PCCT imaging data, in accordance with one or more embodiments.

In one embodiment, at step 106 of FIG. 1, the machine learning based network is trained for performing a plurality of medical imaging analysis tasks based on the one or more PCCT virtual images. FIG. 5 shows a workflow 500 for training a machine learning based network for performing a plurality of medical imaging analysis tasks based on PCCT imaging data, in accordance with one or more embodiments. PCCT imaging data 502, virtual images 504, and ML-based network 506 in FIG. 5 may correspond to PCCT imaging data 202, virtual images 204, and ML-based network 206 in FIG. 2, respectively. As shown in FIG. 5, PCCT imaging data 502 and one or more virtual images 504 are generated from PCCT imaging data 502. ML-based network 506 is jointly trained for performing a plurality of medical imaging analysis tasks 508-A, 508-B, . . . , 508-C (collectively referred to as medical imaging analysis tasks 508), for example, using multi-task learning.

In one embodiment, the machine learning based network is trained at step 106 of FIG. 1 using the raw PCCT imaging data directly. In this embodiment, the intermediate step of generating the PCCT virtual images at step 104 of FIG. 1 can be avoided.

In one embodiment, the raw PCCT imaging data may be reconstructed with various parameters (that could span the space beyond typical clinical reconstructions). The reconstructed PCCT imaging data could be used for augmenting the existing data or for self-supervised pre-training (e.g., during pre-training step 328 of FIG. 3 and/or pre-training step 418 of FIG. 4).

Figure 6:
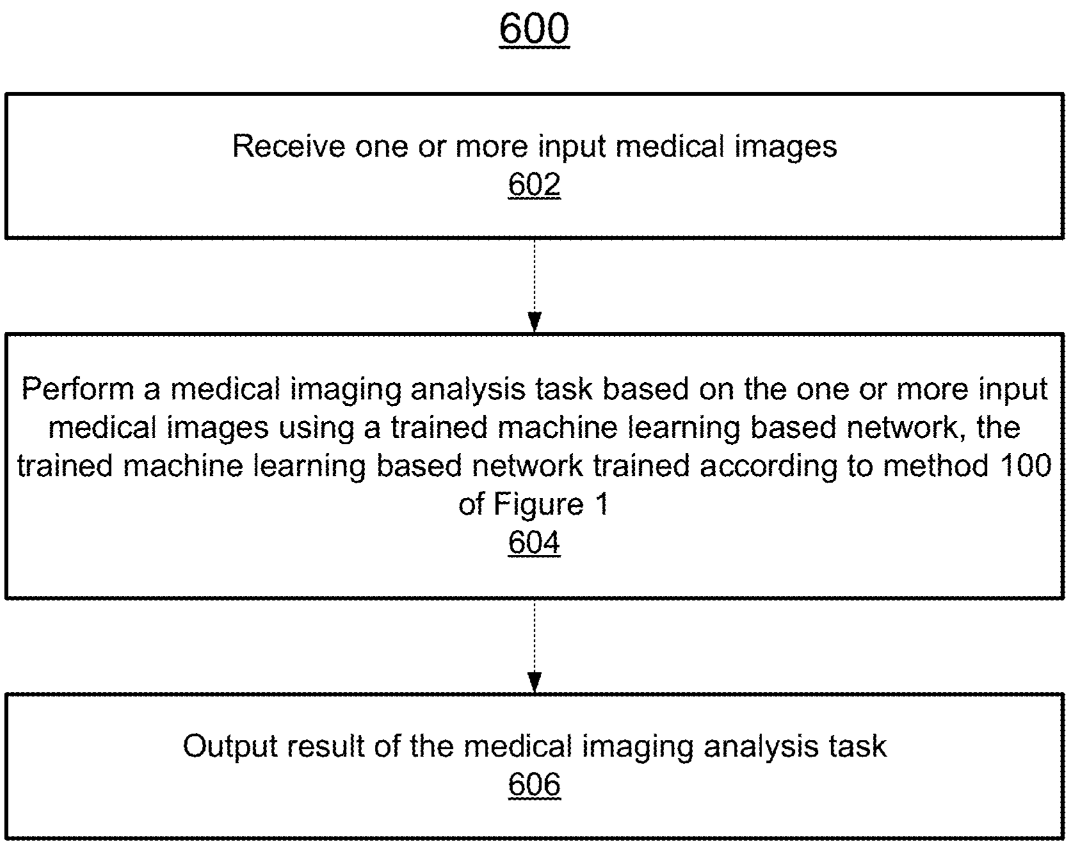
FIG. 6 shows a method for performing a medical imaging analysis task using a trained machine learning based network, in accordance with one or more embodiments.

FIG. 6 shows a method 600 for performing a medical imaging analysis task using a trained machine learning based network, in accordance with one or more embodiments. The steps of method 600 may be performed by one or more suitable computing devices, such as, e.g., computer 902 of FIG. 9.

At step 602, one or more input medical images are received. In one embodiment, the one or more input medical images comprise one or more PCCT virtual images of a patient. However, the one or more input medical images may be of any suitable modality, such as, e.g., CT, MRI, ultrasound, x-ray, or any other medical imaging modality or combinations of medical imaging modalities. The one or more input medical images may be received directly from an image acquisition device, such as, e.g., a CT scanner, as the medical images are acquired, by loading previously acquired medical images from a storage or memory of a computer system, or by receiving medical images from a remote computer system.

At step 604, a medical imaging analysis task is performed based on the one or more input medical images using a trained machine learning based network. In one embodiment, the trained machine learning based network is trained during a prior offline or training stage according to method 100 of FIG. 1. The medical imaging analysis task may comprise any suitable imaging analysis task, such as, e.g., segmentation, detection, registration, etc.

At step 606, results of the medical imaging analysis task are output. For example, the results of the medical imaging analysis task can be output by displaying the results of the medical imaging analysis task on a display device of a computer system, storing the results of the medical imaging analysis task on a memory or storage of a computer system, or by transmitting the results of the medical imaging analysis task to a remote computer system.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based model can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
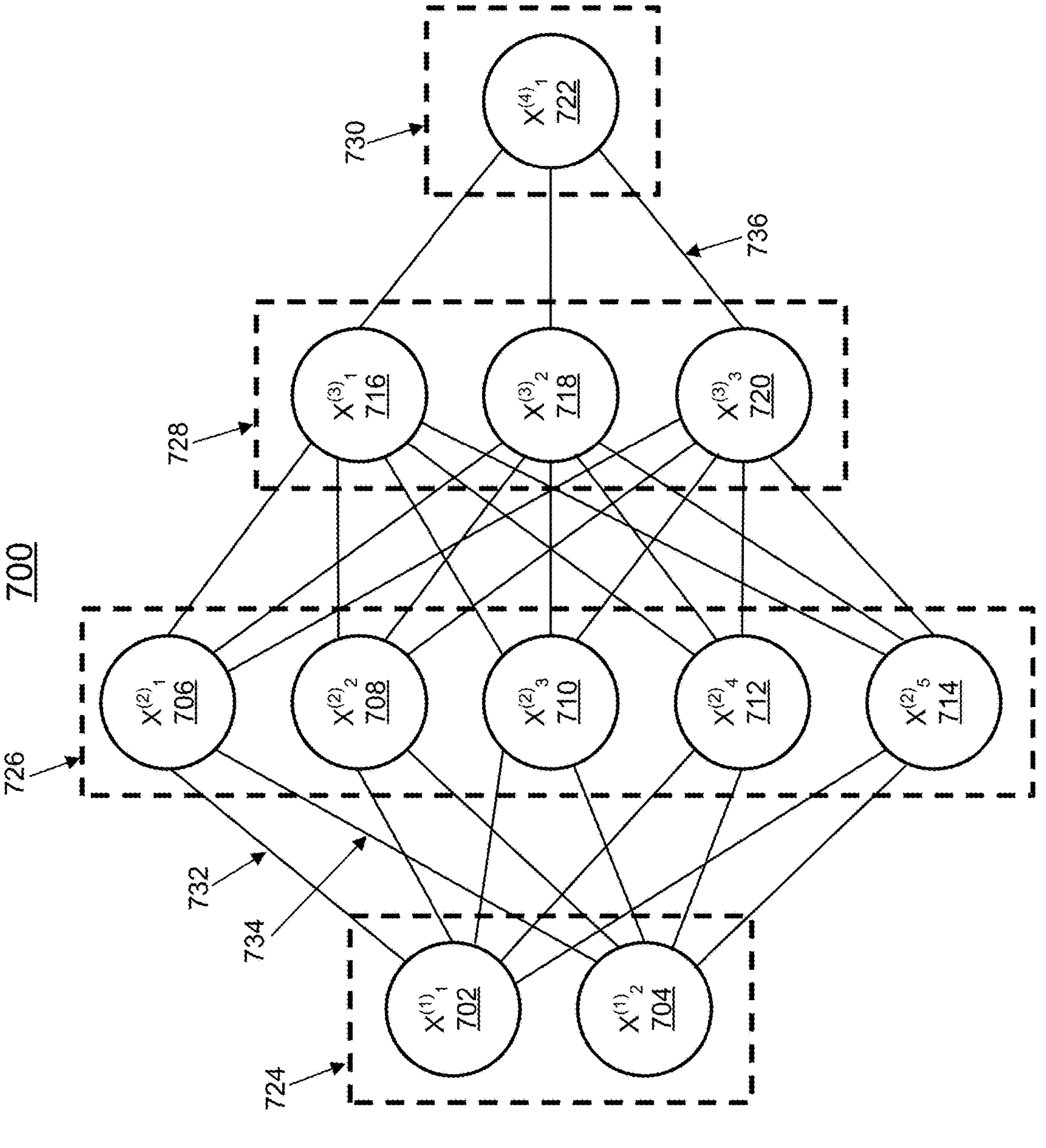
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein, such as, e.g., the machine learning based network of step 106 of FIG. 1, ML-based network 206 of FIG. 2, ML-based network 304 of FIG. 3A, ML-based network 316 of FIG. 3B, ML-based network 324 of FIG. 3C, ML-based network 414 of FIG. 4A, ML-based network 414 of FIG. 4B, ML-based network 506 of FIG. 5, and the trained machine learning based network of step 604 of FIG. 6, may be implemented using artificial neural network 700.

The artificial neural network 700 comprises nodes 702-722 and edges 732, 734, . . . , 736, wherein each edge 732, 734, . . . , 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, . . . , 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, . . . , 736 between the nodes 702-722. In particular, edges 732, 734, . . . , 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}_i$ denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, . . . , 736 can comprise a weight being a real number, in particular, the weight is a real number within the interval [−1, 1] or within the interval [0, 1]. Here, $w^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n,n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_k - t^{(n+1)}_j\right) \cdot f'\left(\sum_i x^{(n)}_i \cdot w^{(n)}_{i,j}\right)$$

if the (n+1)-th layer is the output layer 730, wherein f' is the first derivative of the activation function, and $y^{(n+1)}_j$ is the comparison training value for the j-th node of the output layer 730.

Figure 8:
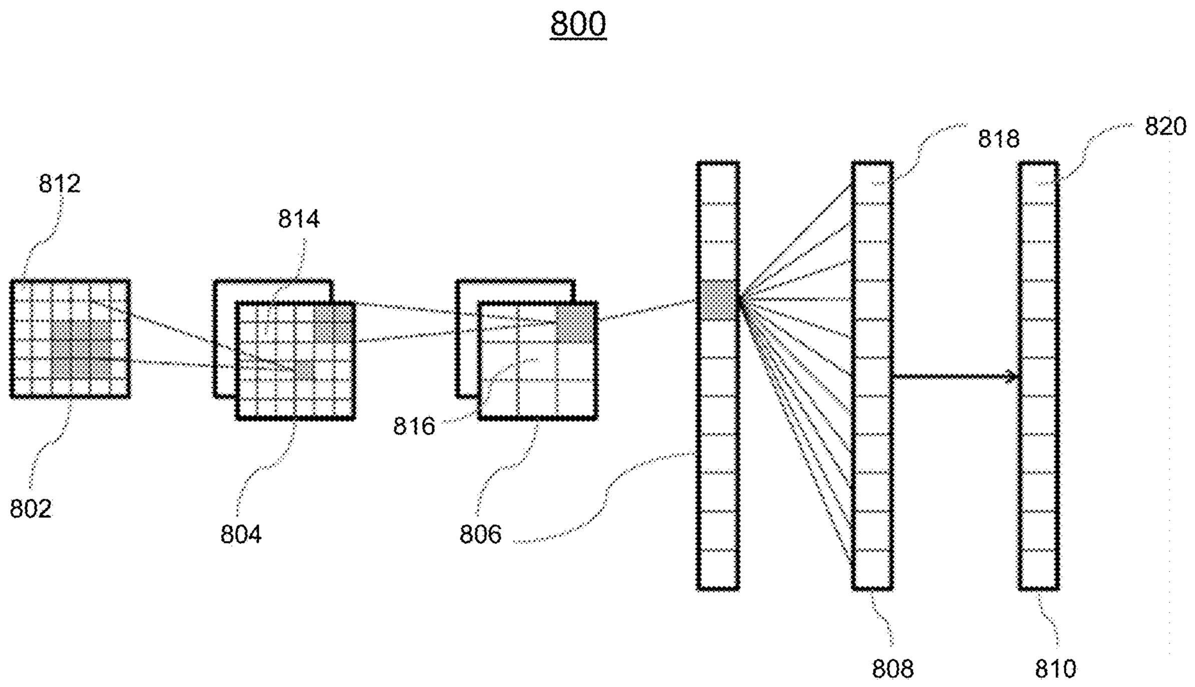
FIG. 8 shows a convolutional neural network that may be used to implement one or more embodiments.

FIG. 8 shows a convolutional neural network 800, in accordance with one or more embodiments. Machine learning networks described herein, such as, e.g., the machine learning based network of step 106 of FIG. 1, ML-based network 206 of FIG. 2, ML-based network 304 of FIG. 3A, ML-based network 316 of FIG. 3B, ML-based network 324 of FIG. 3C, ML-based network 414 of FIG. 4A, ML-based network 414 of FIG. 4B, ML-based network 506 of FIG. 5, and the trained machine learning based network of step 604 of FIG. 6, may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k = K_k * x^{(n-1)}$ based on the values $x^{(n-1)}$ of the nodes 812 of the preceding layer 802, where the convolution * is defined in the two-dimensional case as $$x^{(n)}_k[i,j] = (K_k * x^{(n-1)})[i,j] = \sum_{i'} \sum_{j'} K_k[i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values $x^{(n)}$ of the nodes 816 of the pooling layer 806 can be calculated based on the values $x^{(n-1)}$ of the nodes 814 of the preceding layer 804 as $$x^{(n)}[i,i]=f(x^{(n-1)}[id_1,jd_2], \ldots ,x^{(n-1)}[id_1+d_1-1,jd_2+d_2-1])$$

In other words, by using a pooling layer 806, the number of nodes 814, 816 can be reduced, by replacing a number d1·d2 of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g., dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-6. Certain steps or functions of the methods and workflows described herein, including one or more of the steps or functions of FIGS. 1-6, may be performed by a server or by another processor in a network-based cloud-computing system. Certain steps or functions of the methods and workflows described herein, including one or more of the steps of FIGS. 1-6, may be performed by a client computer in a network-based cloud computing system. The steps or functions of the methods and workflows described herein, including one or more of the steps of FIGS. 1-6, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-6, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
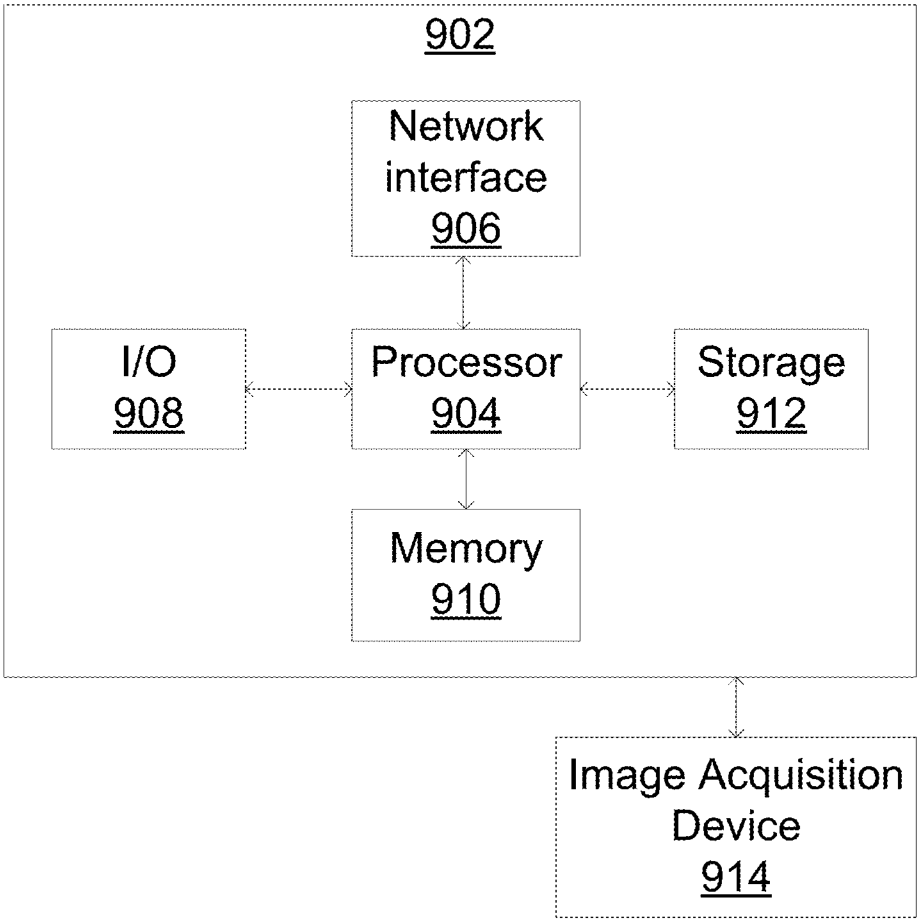
FIG. 9 shows a high-level block diagram of a computer that may be used to implement one or more embodiments.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIGS. 1-6 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 1-6. Accordingly, by executing the computer program instructions, the processor 904 executes the method and workflow steps or functions of FIGS. 1-6. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
- receiving one or more input medical images;
- performing a medical imaging analysis task based on the one or more input medical images using a trained machine learning based network; and
- outputting results of the medical imaging analysis task,
- wherein the trained machine learning based network is trained by:
  - receiving 1) PCCT (photon counting computed tomography) imaging data acquired from a PCCT imaging device and 2) non-photon-counting data, the PCCT imaging data comprising a PCCT virtual image with a first energy level;
  - generating one or more PCCT virtual images by weighting and combining different energy levels in the PCCT imaging data;
  - training the machine learning based network for performing the medical imaging analysis task by:
    - pre-training the machine learning based network based on the non-photon-counting data, and
    - fine-tuning the pre-trained machine learning based network for reconstructing one or more PCCT virtual images with a second energy level based on the PCCT virtual image with the first energy level; and
  - outputting the trained machine learning based network.

2. The computer-implemented method of claim 1, wherein the one or more PCCT virtual images comprise at least one of virtual monoenergetic images, virtual non-contrast images, virtual iodine images, virtual pure lumen images, or ultra-high-resolution images.

3. The computer-implemented method of claim 1, wherein the one or more PCCT virtual images comprises a plurality of PCCT virtual images and training the machine learning based network for performing the medical imaging analysis task comprises:

training the machine learning based network based on a multi-channel image comprising the plurality of PCCT virtual images.

4. The computer-implemented method of claim 1, wherein the one or more PCCT virtual images comprises a plurality of PCCT virtual images, pre-training the machine learning based network based on the non-photon-counting data comprises pre-training the machine learning based network based on a multi-channel image comprising the non-photon-counting data, and fine-tuning the pre-trained machine learning based network based on the one or more PCCT virtual images comprises fine-tuning the pre-trained machine learning based network based on a multi-channel image comprising the plurality of PCCT virtual images.

5. The computer-implemented method of claim 1, wherein training the machine learning based network for performing the medical imaging analysis task comprises:

training the machine learning based network for performing a plurality of medical imaging analysis tasks.

6. An apparatus comprising:

means for receiving one or more input medical images;

means for performing a medical imaging analysis task based on the one or more input medical images using a trained machine learning based network; and means for outputting results of the medical imaging analysis task, wherein the trained machine learning based network is trained by:

receiving 1) PCCT (photon counting computed tomography) imaging data acquired from a PCCT imaging device and 2) non-photon-counting data, the PCCT imaging data comprising a PCCT virtual image with a first energy level;

generating one or more PCCT virtual images by weighting and combining different energy levels in the PCCT imaging data;

training the machine learning based network for performing the medical imaging analysis task by:

pre-training the machine learning based network based on the non-photon-counting data, and fine-tuning the pre-trained machine learning based network for reconstructing one or more PCCT virtual images with a second energy level based on the PCCT virtual image with the first energy level; and outputting the trained machine learning based network.

7. The apparatus of claim 6, wherein the one or more PCCT virtual images comprise at least one of virtual monoenergetic images, virtual non-contrast images, virtual iodine images, virtual pure lumen images, or ultra-high-resolution images.

8. A non-transitory computer readable medium storing computer program instructions, the computer program instructions when executed by a processor cause the processor to perform operations comprising:

receiving one or more input medical images;

performing a medical imaging analysis task based on the one or more input medical images using a trained machine learning based network; and outputting results of the medical imaging analysis task, wherein the trained machine learning based network is trained by:

receiving 1) PCCT (photon counting computed tomography) imaging data acquired from a PCCT imaging device and 2) non-photon-counting data, the PCCT imaging data comprising a PCCT virtual image with a first energy level;

generating one or more PCCT virtual images by weighting and combining different energy levels in the PCCT imaging data;

training the machine learning based network for performing the medical imaging analysis task by:

pre-training the machine learning based network based on the non-photon-counting data, and fine-tuning the pre-trained machine learning based network for reconstructing one or more PCCT virtual images with a second energy level based on the PCCT virtual image with the first energy level; and outputting the trained machine learning based network.

9. The non-transitory computer readable medium of claim 8, wherein the one or more PCCT virtual images comprise at least one of virtual monoenergetic images, virtual non-contrast images, virtual iodine images, virtual pure lumen images, or ultra-high-resolution images.

10. The non-transitory computer readable medium of claim 8, wherein the one or more PCCT virtual images comprises a plurality of PCCT virtual images and training the machine learning based network for performing the medical imaging analysis task comprises:

training the machine learning based network based on a multi-channel image comprising the plurality of PCCT virtual images.

11. The non-transitory computer readable medium of claim 8, wherein the one or more PCCT virtual images comprises a plurality of PCCT virtual images, pre-training the machine learning based network based on the non-photon-counting data comprises pre-training the machine learning based network based on a multi-channel image comprising the non-photon-counting data, and fine-tuning the pre-trained machine learning based network based on the one or more PCCT virtual images comprises fine-tuning the pre-trained machine learning based network based on a multi-channel image comprising the plurality of PCCT virtual images.

12. The non-transitory computer readable medium of claim 8, wherein training the machine learning based network for performing the medical imaging analysis task comprises:

training the machine learning based network for performing a plurality of medical imaging analysis tasks.

13. A computer-implemented method comprising:

receiving 1) PCCT (photon counting computed tomography) imaging data acquired from a PCCT imaging device and 2) non-photon-counting data, the PCCT imaging data comprising a PCCT virtual image with a first energy level;

generating one or more PCCT virtual images by weighting and combining different energy levels in the PCCT imaging data;

training a machine learning based network for performing a medical imaging analysis task by:

pre-training the machine learning based network based on the non-photon-counting data, and fine-tuning the pre-trained machine learning based network for reconstructing one or more PCCT virtual images with a second energy level based on the PCCT virtual image with the first energy level; and outputting the trained machine learning based network.

14. A non-transitory computer readable medium storing computer program instructions, the computer program instructions when executed by a processor cause the processor to perform the steps of claim 13.

* * * * *